(12) United States Patent
Kratoska (10) Patent No.: US 11,517,296 B2
(45) Date of Patent: Dec. 6, 2022

(54) THERMAL MECHANISM TO PREVENT REPROCESSING OR REUSE OF MECHANICAL SURGICAL DEVICES

(71) Applicant: GYRUS ACMI, INC., Southborough, MA (US)

(72) Inventor: William F. Kratoska, Plymouth, MN (US)

(73) Assignee: Gyrus ACMI Inc., Westborough, MA (US)

( * ) Notice: Subject to any disclaimer, the term of this patent is extended or adjusted under 35 U.S.C. 154(b) by 159 days.

(21) Appl. No.: 16/784,655

(22) Filed: Feb. 7, 2020

(65) Prior Publication Data

US 2020/0170631 A1 Jun. 4, 2020

Related U.S. Application Data

(63) Continuation of application No. 15/680,270, filed on Aug. 18, 2017, now Pat. No. 10,555,725.

(Continued)

(51) Int. Cl.
*A61B 17/00* (2006.01)
*A61B 17/28* (2006.01)
(Continued)

(52) U.S. Cl.
CPC .......... *A61B 17/00* (2013.01); *A61B 17/2816* (2013.01); *A61B 17/29* (2013.01);
(Continued)

(58) Field of Classification Search
CPC combination set(s) only.
See application file for complete search history.

(56) References Cited

U.S. PATENT DOCUMENTS

| 4,624,578 A | 11/1986 | Green |
|---|---|---|
| 4,682,435 A | 7/1987 | Heltzel |

(Continued)

FOREIGN PATENT DOCUMENTS

| CN | 1436060 A | 8/2003 |
|---|---|---|
| CN | 201924463 U | 8/2011 |

(Continued)

OTHER PUBLICATIONS

"European Application Serial No. 21183484.1, Extended European Search Report dated Oct. 15, 2021", 7 pgs.

(Continued)

*Primary Examiner* — Gary Jackson
*Assistant Examiner* — Zahed Kabir
(74) *Attorney, Agent, or Firm* — Schwegman Lundberg & Woessner, P.A.

(57) ABSTRACT

A surgical apparatus comprising: a mechanism that is configured to perform an operational motion of the surgical apparatus; and at least one transformation member having an original shape and a deformed shape, the at least one transformation member connecting the mechanism together, when the at least one transformation member is in the deformed shape so that the mechanism is capable of performing the operational motion; and wherein after the transformation member is subject a transition temperature, the at least one transformation member changes from the deformed shape to the original shape and disengages a portion of the mechanism so that the mechanism is prevented from performing the operational motion.

17 Claims, 6 Drawing Sheets

Related U.S. Application Data (60) Provisional application No. 62/401,253, filed on Sep. 29, 2016.

(51) Int. Cl.
*A61B 17/29* (2006.01)
*A61B 90/00* (2016.01)

(52) U.S. Cl.
CPC .. *A61B 17/2909* (2013.01); *A61B 2017/0023* (2013.01); *A61B 2017/00367* (2013.01); *A61B 2017/00867* (2013.01); *A61B 2017/00982* (2013.01); *A61B 2017/2919* (2013.01); *A61B 2090/0814* (2016.02)

(56) References Cited

U.S. PATENT DOCUMENTS

| | | | |
|---|---|---|---|
| 4,781,683 | A | 11/1988 | Wozniak et al. |
| 5,149,322 | A | 9/1992 | Nash |
| 5,563,669 | A | 10/1996 | Stephenson, III |
| 5,946,840 | A | 9/1999 | Mickel |
| 6,158,314 | A | 12/2000 | Thead et al. |
| 6,549,794 | B1 | 4/2003 | Nadeau, Jr. et al. |
| 6,611,793 | B1 | 8/2003 | Burnside et al. |
| 6,808,525 | B2 | 10/2004 | Latterell et al. |
| 6,843,014 | B1 | 1/2005 | Aponte et al. |
| 6,994,314 | B2 | 2/2006 | Garnier et al. |
| 7,118,564 | B2 | 10/2006 | Ritchie et al. |
| 7,204,835 | B2 | 4/2007 | Latterell et al. |
| 7,255,263 | B2 | 8/2007 | Isaacson et al. |
| 7,690,231 | B1 | 4/2010 | Field et al. |
| 7,879,032 | B1 | 2/2011 | Garito et al. |
| 7,998,159 | B2 | 8/2011 | Edwards |
| 8,046,082 | B2 | 10/2011 | Herregraven et al. |
| 8,652,134 | B2 | 2/2014 | Kratoska et al. |
| 9,089,337 | B2 | 7/2015 | Batchelor et al. |
| 9,198,719 | B2 | 12/2015 | Murdeshwar et al. |
| D748,787 | S | 2/2016 | Windgassen et al. |
| 10,555,725 | B2 | 2/2020 | Kratoska |
| 2003/0114839 | A1* | 6/2003 | Looper .......... A61B 17/320016 606/1 |
| 2004/0267254 | A1* | 12/2004 | Manzo ............. A61B 18/14 606/49 |
| 2006/0256664 | A1 | 11/2006 | Varon |
| 2008/0215053 | A1* | 9/2008 | Thomke ............ A61B 17/6466 606/59 |
| 2009/0050253 | A1 | 2/2009 | Thomas et al. |
| 2010/0280511 | A1 | 11/2010 | Rachlin et al. |
| 2010/0298743 | A1 | 11/2010 | Nield et al. |
| 2011/0270179 | A1 | 11/2011 | Ouyang et al. |
| 2011/0301601 | A1 | 12/2011 | Garrison et al. |
| 2012/0191091 | A1 | 7/2012 | Allen |
| 2012/0203224 | A1 | 8/2012 | Kratoska et al. |
| 2013/0046337 | A1 | 2/2013 | Evans et al. |
| 2013/0289559 | A1* | 10/2013 | Reid, Jr. ............ A61B 18/1477 606/41 |
| 2014/0058363 | A1 | 2/2014 | Berkelaar |
| 2014/0200580 | A1 | 7/2014 | Joseph et al. |
| 2015/0051599 | A1 | 2/2015 | Joseph |
| 2017/0000320 | A1 | 1/2017 | Wilson et al. |
| 2018/0085100 | A1 | 3/2018 | Kratoska |

FOREIGN PATENT DOCUMENTS

| | | |
|---|---|---|
| CN | 103347459 A | 10/2013 |
| CN | 107874814 A | 4/2018 |
| CN | 107874814 B | 4/2021 |
| CN | 113143408 A | 7/2021 |
| EP | 3300670 A1 | 4/2018 |
| EP | 3300670 B1 | 7/2021 |
| JP | 2000509636 A | 8/2000 |
| JP | 2004147724 A | 5/2004 |
| JP | 2008100062 A | 5/2008 |
| JP | 2014513563 A | 6/2014 |
| JP | 2018051307 A | 4/2018 |
| JP | 6464239 B2 | 1/2019 |
| WO | WO-9837819 A1 | 9/1998 |
| WO | WO-2016077150 A1 | 5/2016 |

OTHER PUBLICATIONS

"Chinese Application Serial No. 201710831499.4, Office Action dated Jul. 27, 2020", with machine translation, 10 pgs.

"Chinese Application Serial No. 201710831499.4, Response Filed May 7, 2020 to Office Action dated Dec. 25, 2019", w/ English Claims, 12 pgs.

"Chinese Application Serial No. 201710831499.4, Response filed 10-09-0 to Office Action dated Jul. 27, 2020", with machine translation, 14 pgs.

"U.S. Appl. No. 15/680,270, Non Final Office Action dated Jun. 26, 2019", 11 pgs.

"U.S. Appl. No. 15/680,270, Notice of Allowance dated Oct. 8, 2019", 11 pgs.

"U.S. Appl. No. 15/680,270, Response filed Jul. 19, 2019 to Non Final Office Action dated Jun. 26, 2019", 7 pgs.

"Chinese Application Serial No. 201710831499.4, Office Action dated Dec. 25, 2019", w/English Translation, 18 pgs.

"Chinese Application Serial No. 201710831499.4, Voluntary Amendment filed Jul. 24, 2018", with English translation of claims, 13 pgs.

"Different Kinds of Mechanisms", (Sep. 7, 2016), 16 pgs.

"European Application Serial No. 17190058.2, Extended European Search Report dated Feb. 2, 2018", 6 pgs.

"European Application Serial No. 17190058.2, Response filed Sep. 27, 2018 to Extended European Search Report dated Feb. 2, 2018", 18 pgs.

"Japanese Application Serial No. 2017-182610, Notice of Reasons for Rejection dated Jul. 24, 2018", w/ English Translation, 7 pgs.

"Japanese Application Serial No. 2017-182610, Response filed Oct. 12, 2018 to Notice of Reasons for Rejection dated Jul. 24, 2018", with English translation of claims, 11 pgs.

"European Application Serial No. 21183484.1, Response filed Jun. 22, 2022 to Extended European Search Report dated Oct. 15, 2021", 13 pgs.

* cited by examiner

THERMAL MECHANISM TO PREVENT REPROCESSING OR REUSE OF MECHANICAL SURGICAL DEVICES

CROSS-REFERENCE TO RELATED APPLICATIONS

This application is a continuation of U.S. application Ser. No. 15/680,270, filed Aug. 18, 2017, which claims priority to U.S. Provisional Patent Application Ser. No. 62/401,253, filed on Sep. 29, 2016, the contents of which are hereby incorporated by reference in their entireties.

FIELD

The present teachings relate to anti-reuse devices that are part of a device, particularly to surgical devices that include a mechanism to prevent reprocessing or reuse of surgical devices, more particularly to a thermally based mechanism to prevent reprocessing or reuse of mechanical and/or electromechanical surgical devices.

BACKGROUND

Efforts to improve surgical devices, particularly those devices that are typically intended as single use devices (e.g. devices for use on one patient in one procedure, devices not intended for reprocessing after its initial use) have been the pursuit of portions of the medical device industry for decades. These single use devices typically are lower cost than those that are intended to be reprocessed and reused, and are generally designed for a low number of cycles. The devices are specifically marked and approved by local governmental agencies (e.g. FDA) for single use. In some instances, it has been found that some users try to reprocess (e.g. re-sterilize, typically via heating) the device for use with multiple patients, using them for what may be known as "off label" usage. In order to prevent such off label usage, it may be desirable to design devices that that include a mechanism to prevent reprocessing, or at least prevent effective usage of the device after reprocessing or after a set amount of use. Past innovations that have attempted to solve this particular problem have typically been drawn to methods of locking electronic circuits or blocking mechanisms and not as to the innovative manner as in the present teachings disclosed herein.

Examples of single use devices are found in the following patent documents: U.S. Pat. Nos. 8,652,134; 11,576,90231; U.S. Pat. Nos. 5,149,322; 6,843,014; 5,946,840; 7,255,263; and WO/1998/037819; all of which are expressly incorporated herein by reference for all purposes and particularly for teachings on preventing effective usage of the device after reprocessing or after use.

It would be desirable to have a device that includes one or more anti-reuse devices or features that allow one or more parts of the device to fall apart upon heating of the device. What is needed is a transformation member (e.g., an anti-reuse device) that is a pivot pin, joint, track, channel, slider, axis, or a combination thereof that upon heating ceases to hold two or more parts together.

SUMMARY

The present teachings seek to help solve one or more of the problems/issues disclosed above. The present teachings are particularly directed to surgical devices that include a mechanism to prevent reprocessing or reuse of the devices, more particularly to a thermally based mechanism to prevent reprocessing or reuse of mechanical and/or electromechanical surgical devices.

Accordingly, pursuant to one aspect of the present teachings, there is contemplated a surgical apparatus for performing an operation on a patient comprising: a housing for containing a mechanism, the mechanism configured to perform an operational motion of the surgical apparatus; and at least one transformation member; wherein after the transformation member being subject a transition temperature, the transformation member is adapted to disengage a portion of the mechanism and thus prevent the mechanism from performing the operational motion.

The teachings may be further characterized by one or any combination of the features described herein, such as the transformation member is at least partially comprised of a shape-memory material, a pin that moves axially to disengage the portion of the mechanism; the pin is a pivot pin and moving it axially causes at least two relatively pivoting arms to become disengaged from each other; the pin is a catch pin that aligns (a wall or guide) of a guide track such that moving the pin causes the guide track to disengage; the transformation member comprises at least a portion of a guide way; the transformation member comprises at least a portion of a sliding member; the transformation member is configured such that, upon assuming a predetermined shape, at least a portion of the housing falls apart.

The present teachings provide: a surgical apparatus comprising: a mechanism that is configured to perform an operational motion of the surgical apparatus; and at least one transformation member having an original shape and a deformed shape, the at least one transformation member connecting the mechanism together, when the at least one transformation member is in the deformed shape so that the mechanism is capable of performing the operational motion; and wherein after the transformation member is subject a transition temperature, the at least one transformation member disengages a portion of the mechanism so that the mechanism is prevented from performing the operational motion.

The present teachings provide: a surgical apparatus comprising: a mechanism that is configured to perform an operational motion of the surgical apparatus; and at least one transformation member having an original shape and a deformed shape, the at least one transformation member connecting the mechanism together, when the at least one transformation member is in the deformed shape so that the mechanism is capable of performing the operational motion; and wherein after the transformation member is subject a transition temperature, the at least one transformation member changes from the deformed shape to the original shape and disengages a portion of the mechanism so that the mechanism is prevented from performing the operational motion.

The present teachings provide a device that includes one or more anti-reuse devices or features that allow one or more parts of the device to fall apart upon heating of the device. The present teachings provide a transformation member (e.g., an anti-reuse device) that is a pivot pin, joint, track, channel, slider, axis, or a combination thereof that upon heating ceases to hold two or more parts together.

DETAILED DESCRIPTION

The present teachings are an improved surgical device that includes one or more innovative features that prevent successful reprocessing or reuse after reprocessing, particularly after reprocessing with thermal methods. Each relevant component of the device may be described in further detail in the following paragraphs, in the drawings, or in the other patent applications that are incorporated by reference herein for the purposes stated. It should be appreciated that the above referenced aspects and examples are non-limiting, as others exist within the present teachings, as shown and described herein.

The present teachings provide a mechanical device that may preferably be a surgical device, an electromechanical device, or similar device. In particular, the surgical device is intended as a single use device. Exemplary examples include, surgical scissors, forceps, cutting forceps, debriders, stone retrieval devices, and similarly known devices. Additional example devices where the use of the present teachings is contemplated may be described and disclosed in U.S. Pat. Nos. 7,204,835; 9,089,337; 9,198,719; 7,998,159; 6,808,525; and D748787, all of which are expressly incorporated by reference herein for the teachings of the structure of a surgical device.

Of particular interest in the present teachings, is providing for a surgical device that includes one or more features that prevent successful functioning of the device after reprocessing. The present teachings relate to anti-reuse devices. The present teachings relate to providing such features via components, materials, and/or mechanisms that cause at least a portion of a device's active mechanisms to disengage or fall apart under predetermined conditions, thus preventing successful functioning. The present teachings provide a device that prevents reuse of a mechanical device and thus the teachings herein contemplate an anti-use device for any mechanical device but preferably for a surgical device. The anti-reuse device (recited herein as a transformation member) may function to disable all or a portion of a mechanical device upon the device obtaining a transformation temperature. The mechanical device may include a housing that surrounds or includes one or more and preferably all of the components.

A housing may function to contain some or all components and/or mechanisms of the device. The housing may function as a simple cover for the components/mechanisms, or be an integral part (e.g. function as a pivot, pivot bearing, or guide track). Some devices contemplated herein, do not require a separate housing, for example a simple pair of scissors may not, and the housing is the blade/handle itself. The device may be free of a housing. The housing may include an internal cavity. The housing may be made of metal or plastic. The housing may be connected to one or more parts of the mechanism. The housing may be free of contact with the mechanism. The housing may be connected to a transformation member and when the transformation member transforms (e.g., changes from deformed shape to original shape) at least a portion of the housing may fall apart. The housing may surround or cover one or more parts of the housing.

A mechanism may function to allow movement of different components of the device, particularly movement in response to eternal stimulus (e.g. user squeezing the handle or moving a lever). The mechanism may be a simple pivot, or something more complex such as, but not limited to: multiple pivoting arms, guide tracks, crank, bell crank, slider-crank, bevel gear, spur gear, cams, universal joint, roller chain, piston, rack and pinion, 3 bar link, 4 bar link, or any combination thereof (see https:/www.scribd.com/doc/28792501/Different-Kinds-of-Mechanisms, accessed on Sep. 7, 2016 and incorporated by reference). The mechanism upon a stimulus may pivot, rotate, slide, or a combination thereof. The mechanism may include one or more of links, sliding members, stationary members, transformation members (acting as one or more of the parts of the mechanism), pivot pin, guideway, crank, connecting rod, connection, bevel gear, gear, universal joint, shaft, cross journal, or a combination thereof. The present teachings are directed at providing a way to cause the disengagement, at least under certain conditions. Preferably, at least a portion of the mechanism is connected together or allowed to operate due to the transformation member and preferably a transformation member in a deformed shape.

The transformation member may be a single unitary piece or an assembly of dissimilar components. The transformation member may function to change between an original shape and a deformed shape. The transformation member may function to connection two or more parts of the mechanism together. The transformation member may have a deformed shape and an original shape. The transition member may be sufficiently rigid and durable so that the device retains is shape and configuration during the duration of use. The transition member may change from a deformed shape to an original shape when subjected to a transition temperature. The transition member may render the device and preferably the surgical device inoperable when the transformation member is in the original shape. Preferably, the transformation member connects two or more parts together when the transformation member is in the deformed shape. The transformation member may be free of holding two or more components together when the transformation member is in the original shape. All or a portion of the transformation member may be comprised of a shape-memory material such as Nitinol, a relatively low melting point material such as Polycaprolactone (PCL) or a similarly low melting polymer, or a wax material. The transformation member may partially or entirely be made of a shape-memory material, a low melting point material, or both. The transformation member may be a portion of a guide way, a sliding member, or both. The transformation member may have a working portion and a pivot pin. The working portion, the pivot pin, or both may be made of a shape-memory material.

The working portion functions as the portion that disengages or causes disengagement of the mechanism when a transition temperature condition is met. The working portion may extend on one or both sides of a recess in a mechanism. The working portion may be the portion that deforms, melts, changes shape, or a combination thereof. The working portion may be connected to another part of the mechanism. The working portion may be connected to the housing (e.g., at a connection). The working portion may be a shape-memory material. The working portion may be free of shape-memory material and the pivot pin may be made of a shape-memory material, a low melting polymer, a wax material, or a combination thereof and may deform or change shape upon being subjected to a transition temperature. The working portion may be flat, planar, or both. The working portion may have one or more contours, one or more bends, one or more arcs, or a combination thereof. The working portion when flat in the deformed shape may move to an arcuate shape when the working portion moves to an original shape. The working portion when may be arcuate when in the deformed shape and may move to a flat shape when the working portion moves to an original shape. The working portion may be generally U shaped or C shaped. The working portion may be the only part of the transformation member. The working portion may create a guide way, a channel, or both that allows a sliding member to slide along. The working portion may have a part that moves and a part that is static. The working portion may axially move a pivot pin.

The pivot pin may function to extend into a recess to connect two or more pieces together. The pivot pin may function to move one component with another component. Two or more parts of the mechanism may rotate about the pivot pin. Two or more parts may axially move, laterally move, longitudinally move, or a combination thereof by a connection formed by the pivot pin. The operational movement may be rotational movement, lateral movement, axial movement, lateral movement, or a combination thereof. The pivot pin may allow for movement in two directions and prevent movement in one direction. For example, the pin may allow for movement in the X and Y direction and prevent movement in the Z movement. The pivot pin may axially move, be axially moved, or both when the transformation member is subjected to the transition temperature. The pivot pin may melt, deform, soften, or a combination thereof when subjected to the transition temperature. The pivot pin may change from a deformed shape to an original shape when subjected to the transition temperature so that the pivot pin no longer constrains one or more parts of the mechanism. The pivot pin upon axially movement may cause at least two relatively pivoting arms of the mechanism to become disengaged from each other. The pivot pin may be a catch pin. The catch pin may align the one or more transformation members with a guide, a wall, a guide track, or a combination thereof of the mechanism that the catch pin moves along. The pin, the guide track, or both may disengage upon being subjected to a transition temperature so that the wall, guide, guide track, pin, or a combination thereof are no longer connected and the mechanism is no longer capable of performing the operational motion. The transformation member may be free of a pivot pin. The transformation member may have all or a portion that is made of a shape-memory material.

Shape-memory materials/components, also known as shape-memory alloy (SMA, smart metal, memory metal, memory alloy, muscle wire, smart alloy) is an alloy that "remembers" its original shape (predetermined shape) and that when deformed returns to its pre-deformed shape when heated to a transition temperature (e.g. as may typically be seen in thermal reprocessing conditions). The transition temperature may be a temperature experienced by an autoclave. The transition temperature of the composition of the shape-memory material may be varied based upon a heating temperature, type of use, manufacturing process to create the device, or a combination thereof. Preferably, the transition temperature is sufficiently high so that the shape-memory materials/components do not transform during a surgical procedure (e.g., in the surgical room). The transition temperature may be sufficiently high so that the shape-memory materials/components are completely deformed, partially deformed, disable one or more functions of a device, completely disable a device, or a combination thereof. The transition temperature may be varied ±5° C. or more, ±10° C. or more, or even about ±20° C. or more than the transition temperatures taught herein. The transition temperature may be about 25° C. or more, about 30° C. or more about 35° C. or more, about 40° C. or more, about 45° C. or more, about 600 or more, or about 100° C. or less. Preferably, the transition temperature is about 100° C. or more, about 125° C. or more, about 150° C., about 175° C. or more, about 200° C. or more, or about 250° C. or less. The transition temperature may be between about 25° C. and 250° C., preferably between about 30° C. and 150° C., or more preferably between about 35° C. and about 50° C. One example of a shape-memory alloy that is sometimes used in surgical devices is Nitinol. A material with such memory properties to enable the functional aspect of disengagement of the mechanism, or at least a portion of the mechanism via a transformation member. A transition temperature may be defined as the temperature or time and temperature that is required to make a given shape-memory material/component return to its pre-deformed shape. The transformation member may include a portion that is a polycaprolactone (PCL) or a degradable portion.

PCL is a biodegradable polyester with a low melting point of around 60° C. and a glass transition temperature of about −60° C. The most common use of polycaprolactone is in the manufacture of specialty polyurethanes. Polycaprolactones impart good water, oil, solvent and chlorine resistance to the polyurethane produced. A transition temperature may be defined as the temperature or time and temperature set forth herein or that is required to soften the PCL such that the working portion functionally disengages or causes disengagement of the mechanism, typically at about 60° C. over at least one or more minutes.

This polymer is often used as an additive for resins to improve their processing characteristics and their end use properties (e.g., impact resistance). Being compatible with a range of other materials, PCL can be mixed with starch to lower its cost and increase biodegradability or it can be added as a polymeric plasticizer to PVC.

In certain instances, it may be advantageous to include a component or feature that functions to prevent the transformation member from returning to the original shape in the case of a shape-memory component or to move/melt away in the case of a polymer, herein referred to as a preload component. In a preferred embodiment, the pre-load component is removable, and particularly removable prior to the first use of the device. As an example, when a surgical device 2 is first assembled and prior to first use in a patient, the device may be subjected to some kind of thermal event (e.g. sterilization or stowage conditions). In such a case, a preload member prevents the transformation member from disengaging the mechanism before the intended time. The preload component may be constructed of any appropriate material, such as metals, polymers, or ceramics. It may be in the form of a pin, wire, flat or shaped plate, or any similar construction that allows it to functionally support the transformation member during the thermal event. The transformation member may connect two or more parts of a mechanism together.

The parts of the mechanism connected together may be two arms; a handle or button and sliding member; two gears; a cross journal and a shaft; a crank and a connecting rod, two links; a crank and a stationary member; a connecting rod and a sliding member; or a combination thereof. Each of the parts of the mechanism may include a recess. The recess may be a through hole. The recess may be a depression in a part. The recess may extend partially into a part of the mechanism so that the mechanism may be pushed or pulled by the transformation member.

Figure 1:
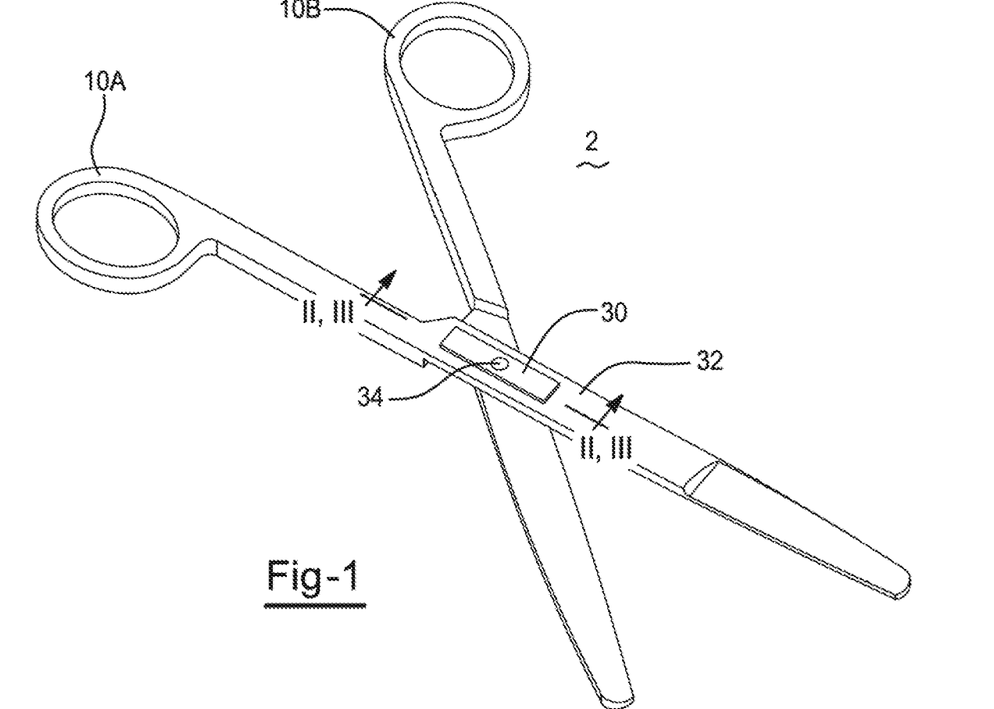
FIG. 1 illustrates a plan view of a surgical device.
Figure 2:
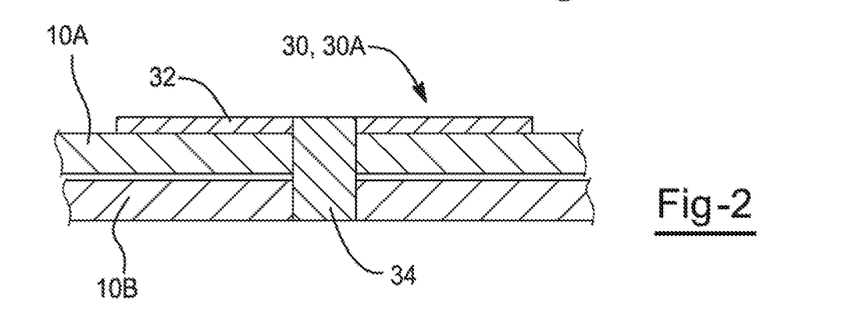
FIG. 2 is a cross-sectional view of FIG. 1 with a transformation member in a deformed shape.
Figure 3:
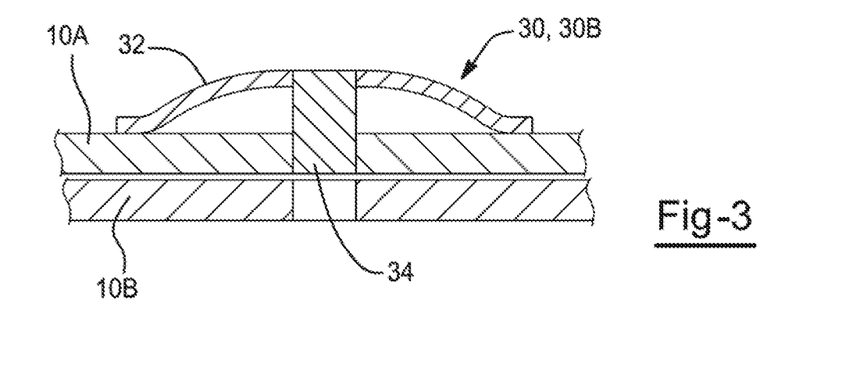
FIG. 3 is a cross-sectional view of FIG. 1 with a transformation member in an original shape.

FIGS. 1, 2, and 3 show an example of a device 2 that is a surgical scissor. The device 2 includes a housing 10 (in this case, the two arms, 10A and 10B), and a transformation member 30. The member 30 is an assembly of a working portion 32 and a pivot pin 34.

FIG. 2 is a cross-sectional view of the device 2 of FIG. 1 with the member 30 shown in a deformed shape 30A, and FIG. 3 is a cross-sectional view of the device 2 of FIG. 1 shown in an original shape 30B (predetermined shape). The transformation member 30 includes a working portion 32 and a pivot pin 34 that extends into holes in the housing 10A, 10B. The holes in the housing 10A, 10B being a bearing surface/interface for the pivot pin 34.

In FIG. 3, the working portion 32 has returned to (or nearly to) its original shape after being subjected to a transition temperature and the transformation member 30 has disengaged the mechanism 20 at the 10B interface so that the pivot pin 34 is removed from one or both holes in the arms of the housing 10A, 10B such that the arms of the housing 10A, 10B are not connected.

Figures 4, 5A, 5B, 5C:
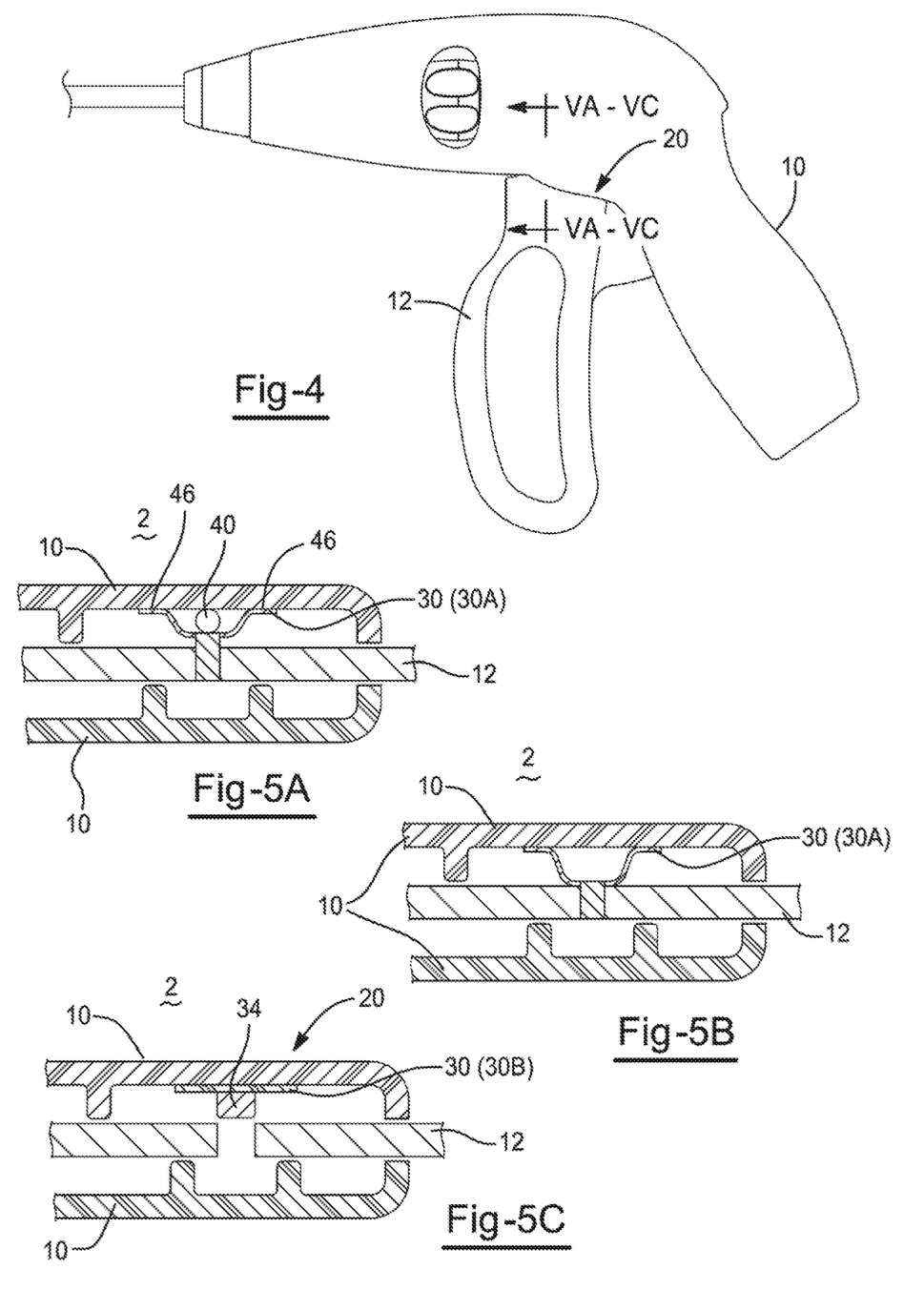
FIG. 4 illustrates a plan view of a surgical device.
FIG. 5A is a cross-sectional view of FIG. 4 with a transformation member in a deformed shape and including a pre-load component.
FIG. 5B is a cross-sectional view of FIG. 4 with a transformation member in a deformed shape.
FIG. 5C is a cross-sectional view of FIG. 4 with a transformation member in an original shape.

FIGS. 4 through 5C illustrate a transformation member 30 that changes to an original flattened shape (versus FIGS. 2 and 3 that change to an original contoured shape). The surgical device 2 of FIG. 4 is a cutting forceps (for example HALO (Hand Activation for Laparoscopy & Open) PKS Cutting Forceps as commercially available from Olympus). The device 2 includes a housing 10, a handle 12, and a mechanism 20 (handle 12 pivoting about pin (not shown)).

FIG. 5A is a cross-sectional view of the device 2 of FIG. 4 with a pre-load component 40. The pre-load component 40 is situated between the housing 10 and the transformation member 30. In this configuration, the preload component 40 acts to maintain the transformation member 30 in its deformed shape 30A and prevent the member 30 from returning to its original shape (not shown) if any transition temperature is experienced. The preload component 40 is removed prior to a first use of the device 2. The component 40 is in the form of a pin and is removable. The transformation member 30 is connected to the housing 10 at a connection 46 that maintains the relationship between the housing 10 and the transformation member 30.

In FIG. 5B, the device 2 is shown as in FIG. 5A with the preload component 40 removed.

In FIG. 5C, the mechanism 20 (a portion thereof) has been disengaged form the device 2 after the transformation member 30 has been subject a transition temperature, and the transformation member 30 has disengaged a portion of the mechanism (pivot pin 34 from handle 12) and thus prevent the mechanism 20 from performing an operational motion.

FIGS. 6, 7, and 8A, 8B show a device 2 with a housing 10 and a sliding handle 12 or button 14 that acts as an input portion of the mechanism 20 that moves a linearly sliding shaft 22 when a transformation member 30 connects the mechanism 20 to the linearly sliding shaft 22.

Figure 6:
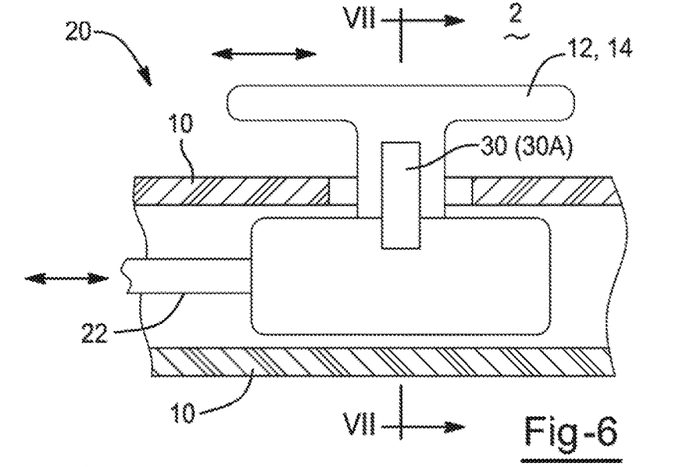
FIG. 6 is a side view of a connection between a button or handle and a sliding shaft of a surgical device that are connected by a transformation member that is in a deformed shape.

FIG. 6 illustrates a side view of a surgical device 2. The surgical device 2 includes a handle 12 or button 14 that is connected to a linearly sliding shaft 22 by a transformation member 30 that is in a deformed shape 30A. The linearly sliding shaft 22 is movable within a housing 10 with arrows showing the relative motion.

Figure 7:
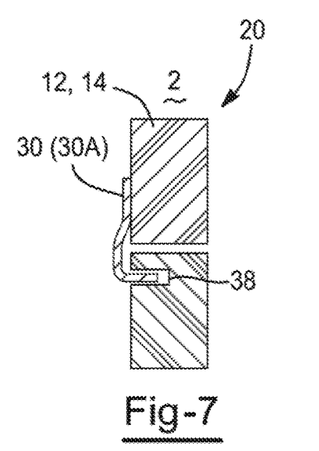
FIG. 7 is a cross-sectional view of FIG. 6.

FIG. 7 illustrates a cross-sectional view of the surgical device 2 of FIG. 6 along line VII-VII. The handle 12 or button 14 is connected to the linearly sliding shaft 22 by the transformation member 30 extending into a recess 38 so that movement of the handle 12 or button 14 moves the linearly sliding shaft 22.

Figure 8A:
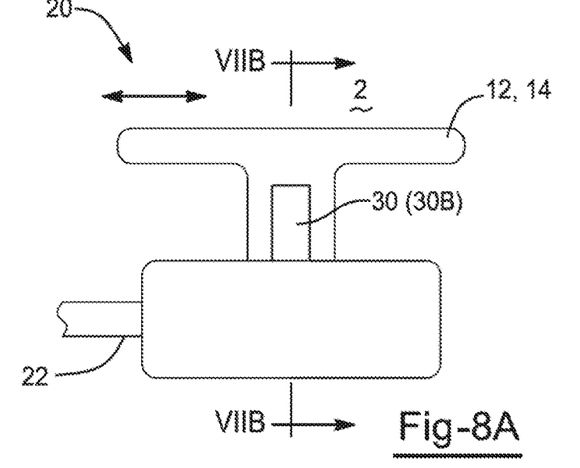
FIG. 8A is a side view of a button or handle and sliding shaft with the transformation member in an original shape so that the button and shaft are not connected.

FIG. 8A is a side view of the surgical device 2 including a mechanism 20 with the handle 12 or button 14 disconnected from the linearly sliding shaft 22 by the transformation member 30 being subjected to a transition temperature so that the transformation member 30 reverts to an original shape 30B. The arrows show the motion of the handle 12 or button 14 relative to the linearly sliding shaft 22.

Figure 8B:
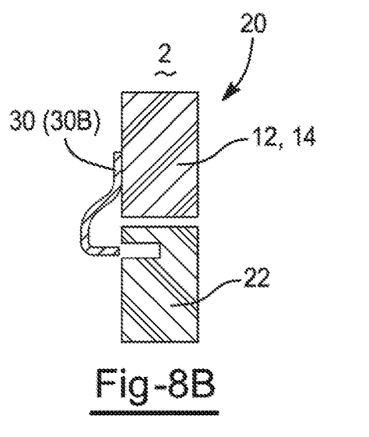
FIG. 8B is a cross-sectional view of FIG. 8A.

FIG. 8B illustrates a cross-sectional view of the surgical device 2 of FIG. 8A along line VIIIB-VIIIB. As shown, the transformation member 30 moves to the original shape 30B when subjected to a transformation temperature so that the transformation member 30 moves out of the recess 38 of the mechanism 20. The transformation member 30 no longer connects the handle 12 or button 14 to the linearly sliding shaft 22 when the transformation member 30 moves out of the recess 38.

Figure 9A:
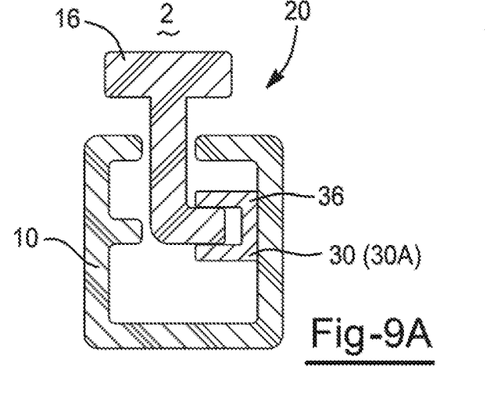
FIG. 9A is a cross-sectional view of a sliding member connected to a housing by a transformation member that is in a deformed shape.
Figure 9B:
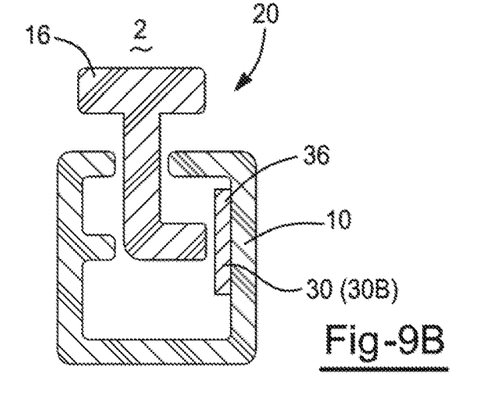
FIG. 9B is a cross-sectional view of the transformation member of FIG. 9A in an original shape so that the sliding member is not constrained by the transformation member.
Figures 10A, 10B:
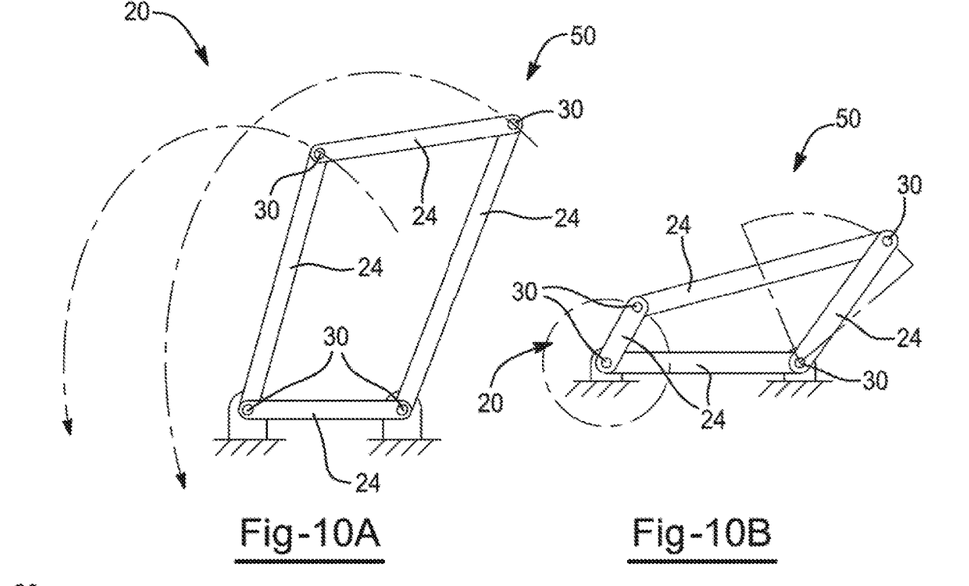
FIGS. 10A, 10B, 10C, and 10D illustrate 4 bar mechanisms and shapes of 4 bar mechanisms.
Figures 10C, 10D:
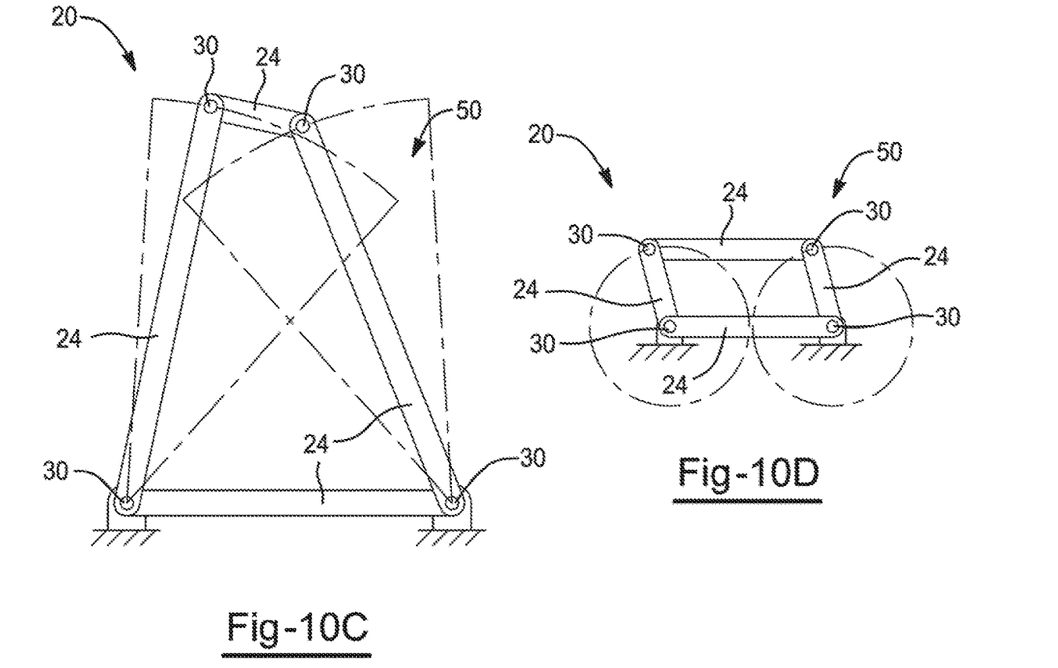

FIGS. 9A and 9B show a device 2 that has a mechanism 20 that has a sliding member 16 that operationally moves fore and aft within a guideway 36. The guideway 36 comprising the transformational member 30. FIG. 9A showing the member in its deformed shape 30A and functionally acting as a guideway or track 36 for the sliding member 16 to move along. FIG. 9B shows the guideway 36 in its original shape 30B after being subject to a transition temperature and no longer acting as a guideway or track, thus allowing disengagement of the mechanism 20.

FIGS. 10A-10D illustrate various 4 bar mechanisms 50 with different shapes. Each 4 bar mechanism 50 includes a mechanism 20 having links 24 that are connected together by transformation members 30 that allow the links 24 to move relative to each other.

Figure 11:
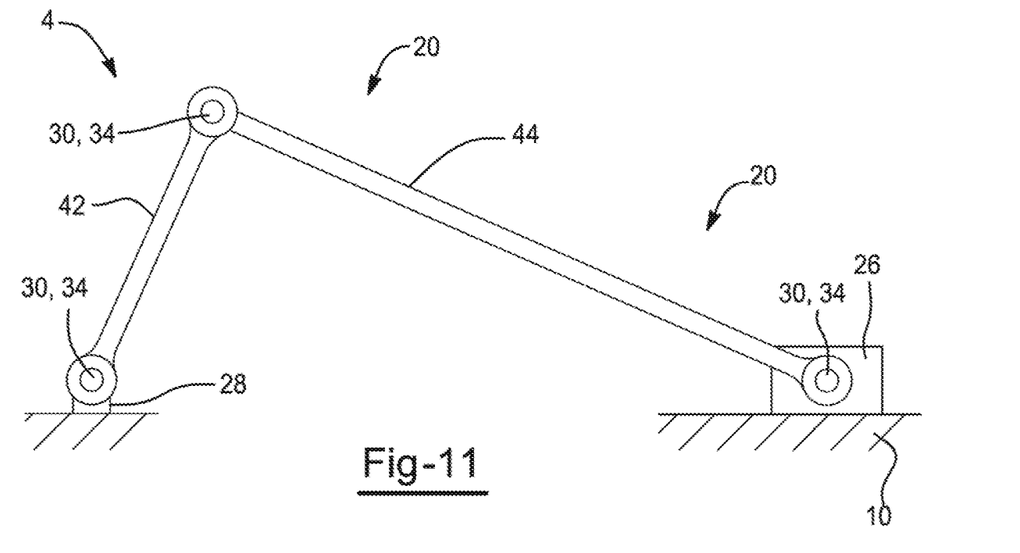
FIG. 11 is a side view of a slider crank.

FIG. 11 illustrates a slider crank 4 that is a mechanism 20. The slider crank includes one end that is a stationary member 28 connected to a housing 10 and a second end that is a sliding member 26 that moves along the housing 10. The stationary end 28 is connected to a crank 42 via a pivot pin 34 that may be a transformation member 30. The crank 42 is connected to a connecting rod 44 by a pivot pin 34 that may be a transformation member 30. The connecting rod 44 is connected to a sliding member 26 by a pivot pin 34 that may be a transformation member 34. When the transformation member 30 is in a deformed state the sliding member 26 is moved along the housing and when one or more of the transformation member 30 are subjected to a transformation temperature the pivot pins prevent movement of the sliding member 26.

Figure 12:
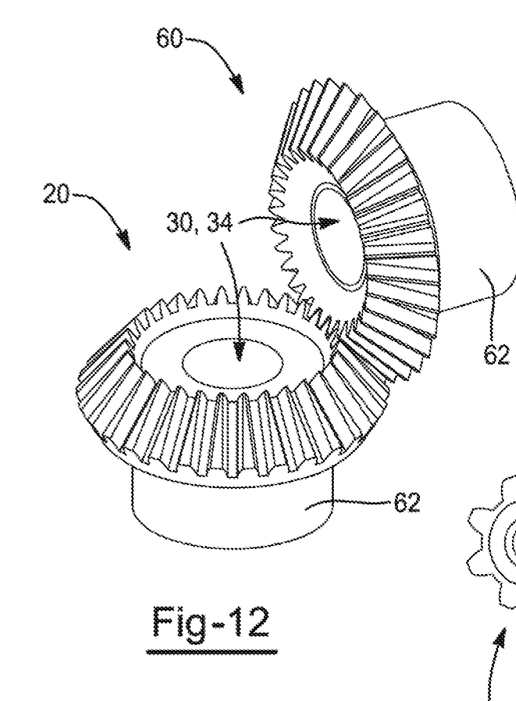
FIG. 12 is a perspective view of a bevel gear.

FIG. 12 illustrates a bevel gear 60, which is a mechanism 20, including two gears 62 that each pivot about a pivot pin 34. One or both of the pivot pins 34 may be a transformation member 30 that when subjected to a transformation temperature reverts back to an original shape so that the bevel gear 60 no longer functions.

Figure 13:
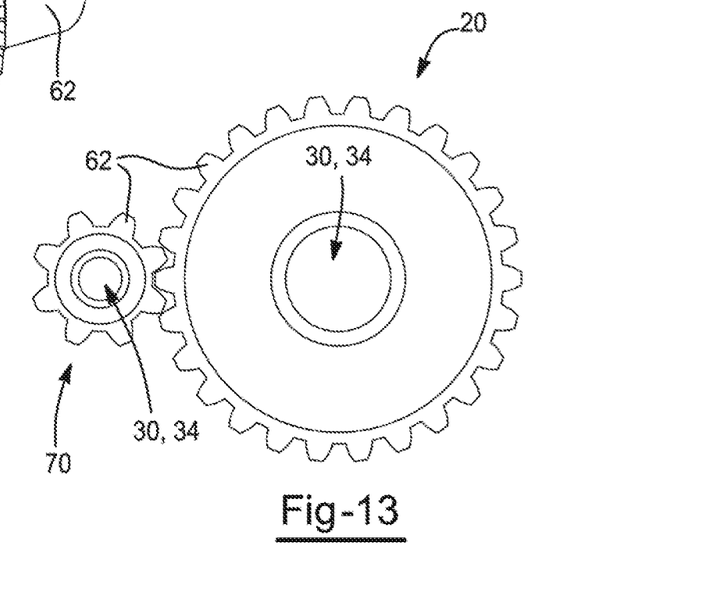
FIG. 13 is a plan view of a spur gear.

FIG. 13 illustrates a spur gear 70, which is a mechanism 20, including two gears 62 that each pivot about a pivot pin 34. One or both of the pivot pins 34 may be a transformation member 30 that when subjected to a transformation temperature reverts back to an original shape so that the spur gear 70 no longer functions.

Figure 14:
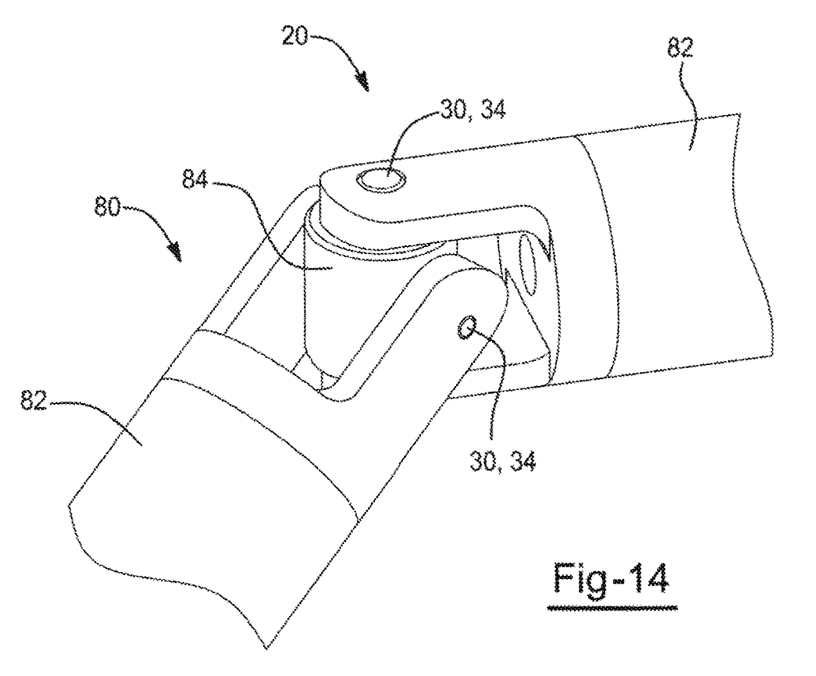
FIG. 14 is a perspective view of a universal joint.

FIG. 14 illustrates a universal joint 80, which is a mechanism 20, including two shafts 82 that are connected together via a cross-journal 84 and pivot pins 34. One or both of the pivot pins 34 may be a transformation member 30 that when subjected to a transformation temperature reverts back to an original shape so that the universal joint 80 no longer functions.

It is contemplated and expressly stated herein that the embodiments or examples described above may not be mutually exclusive and may be used in combination with each other.

Unless stated otherwise, dimensions and geometries of the various structures depicted herein are not intended to be restrictive of the teachings, and other dimensions or geometries are possible. Plural structural components can be provided by a single integrated structure. Alternatively, a single integrated structure might be divided into separate plural components. In addition, while a feature of the present teachings may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present teachings.

The preferred embodiment of the present teachings has been disclosed. A person of ordinary skill in the art would realize however, that certain modifications would come within the teachings of this teachings. Therefore, the following claims should be studied to determine the true scope and content of the teachings.

Any numerical values recited in the above application include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes.

The term "consisting essentially of" to describe a combination shall include the elements, ingredients, components or steps identified, and such other elements ingredients, components or steps that do not materially affect the basic and novel characteristics of the combination.

The use of the terms "comprising" or "including" describing combinations of elements, ingredients, components or steps herein also contemplates embodiments that consist essentially of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps. All references herein to elements or metals belonging to a certain Group refer to the Periodic Table of the Elements published and copyrighted by CRC Press, Inc., 1989. Any reference to the Group or Groups shall be to the Group or Groups as reflected in this Periodic Table of the Elements using the IUPAC system for numbering groups.

The invention claimed is:

1. A surgical apparatus comprising:
   a mechanism that is configured to perform an operational motion of the surgical apparatus, the mechanism including a sliding member that operationally moves fore and aft within a guideway; and
   at least one transformation member partially comprised of a shape-memory material and being at least a portion of the guideway, wherein, when the portion of the guideway is subject to a transition temperature, the portion of the guideway disengages with the sliding member and prevents the mechanism from performing the operational motion.

2. The surgical apparatus according to claim 1, wherein the at least one transformation member has an original shape and a deformed shape.

3. The surgical apparatus according to claim 2, wherein, when the at least one transformation member is in the deformed shape, the mechanism is capable of performing the operational motion.

4. The surgical apparatus according to claim 2, wherein, when the at least one transformation member is in the original shape, the mechanism is prevented from performing the operational motion.

5. The surgical apparatus according to claim 1, wherein the at least one transformation member is at least a portion of the sliding member.

6. The surgical apparatus according to claim 1, wherein the at least one transformation member includes a pin that moves axially to disengage the portion of the mechanism.

7. The surgical apparatus according to claim 6, wherein the pin is a catch pin that aligns a guide of a guide track of the mechanism and moving the pin causes the guide track to disengage so that the mechanism is no longer capable of performing the operational motion.

8. The surgical apparatus according to claim 1, wherein, when subjected to the transition temperature, the at least one transformation member transitions from a deformed shape to an original shape and renders the surgical apparatus inoperable.

9. The surgical apparatus of claim 1, wherein the transition temperature is between about 25 degrees Celsius and about 250 degrees Celsius.

10. A surgical apparatus comprising:
a mechanism that is configured to perform an operational motion of the surgical apparatus, the mechanism including a sliding member that operationally moves fore and aft within a guideway; and
at least one transformation member having a first shape and a second shape, the at least one transformation member connecting the mechanism together and being at least a portion of the guideway,
wherein, when the at least one transformation member is in the first shape, the mechanism is capable of performing the operational motion, and
wherein, when the portion of the guideway is subjected to a transition temperature, the portion of the guideway transitions from the first shape to the second shape and disengages with the sliding member so that the mechanism is prevented from performing the operational motion.

11. The surgical apparatus of claim 10, wherein a portion of the at least one transformation member is at least partially comprised of a shape-memory material.

12. The surgical apparatus of claim 11, wherein the second shape is an original shape and the first shape is a deformed shape.

13. The surgical apparatus of claim 10, wherein a portion of the at least one transformation member is at least partially comprised of a polymer, and wherein the transition temperature of the polymer being about 60 degrees Celsius.

14. The surgical apparatus of claim 13, wherein the second shape is where a portion of the at least one transformation member has melted away.

15. A method of forming a surgical apparatus, the method comprising:
deforming at least a portion of at least one transformation member from an original shape to a deformed shape, the at least one transformation member connecting a mechanism together that is configured to perform an operational motion of the surgical apparatus, the mechanism including a sliding member that operationally moves fore and aft within a guideway wherein the at least one transformation member is at least a portion of the guideway; and
assembling the mechanism of a surgical apparatus that is configured to perform the operational motion of the surgical apparatus, wherein, when the at least one transformation member is in the deformed shape, the mechanism is capable of performing the operational motion and wherein when the at least one transformation member is subject to a transition temperature, the portion of the guideway disengages with the sliding member and prevents the mechanism from performing the operational motion.

16. The method of claim 15, wherein, after the at least one transformation member is subject to a transition temperature, the at least one transformation member transitions from the deformed shape to the original shape.

17. The method of claim 15, wherein the at least one transformation member is at least a portion of the sliding member.

* * * * *

UNITED STATES PATENT AND TRADEMARK OFFICE
CERTIFICATE OF CORRECTION

PATENT NO. : 11,517,296 B2
APPLICATION NO. : 16/784655
DATED : December 6, 2022
INVENTOR(S) : William F. Kratoska It is certified that error appears in the above-identified patent and that said Letters Patent is hereby corrected as shown below:

On the Title Page

In item (73), in "Assignee", in Column 1, Line 1, after "ACMI", insert --,--

Signed and Sealed this
Third Day of October, 2023

Katherine Kelly Vidal
*Director of the United States Patent and Trademark Office*